(12) United States Patent
Tokitoh (10) Patent No.: US 6,929,787 B2
(45) Date of Patent: Aug. 16, 2005

(54) COMPOSITE AND MANUFACTURING METHOD THEREOF

(75) Inventor: Yasuo Tokitoh, Okayama-ken (JP)

(73) Assignee: Kuraray Co., Ltd., Kurashiki (JP)

( * ) Notice: Subject to any disclaimer, the term of this patent is extended or adjusted under 35 U.S.C. 154(b) by 159 days.

(21) Appl. No.: 10/073,225

(22) Filed: Feb. 13, 2002

(65) Prior Publication Data

US 2002/0111269 A1 Aug. 15, 2002

(30) Foreign Application Priority Data

Feb. 13, 2001 (JP) ........................................ 2001-035649

(51) Int. Cl.[7] .............................................. C01B 31/34
(52) U.S. Cl. .................................... 423/440; 423/327.1
(58) Field of Search ........................... 423/327.1, 328.1, 423/345, 439, 440

(56) References Cited

U.S. PATENT DOCUMENTS

| | | | |
|---|---|---|---|
| 3,926,855 A | | 12/1975 | Vesely |
| 3,928,485 A | | 12/1975 | Nagase et al. |
| 5,510,550 A | * | 4/1996 | Cheung et al. ............. 585/259 |
| 5,811,611 A | * | 9/1998 | Hamamatsu et al. ........ 585/438 |
| 6,064,560 A | * | 5/2000 | Hirahara et al. ............ 361/502 |

FOREIGN PATENT DOCUMENTS

| | | |
|---|---|---|
| CN | 1026241 C | 10/1994 |
| CN | 1057277 C | 10/2000 |
| EP | 0 279 397 | 8/1988 |
| EP | 0 664 277 | 7/1995 |
| EP | 0 789 010 | 8/1997 |
| GB | 812526 | 4/1959 |
| JP | 49-123490 | 11/1974 |

OTHER PUBLICATIONS

Supplementary Volume to Shokubai Koza (Catalytic Course), Catalytic Experiment Handbook, edited by Catalysis Society of Japan, vol. 11, pp. 15–17, 1986 (with partial English translation).
A. C. Cope, et al., J. Am. Chem. Soc., vol. 82, pp. 1750–1753, "Acid–Catalyzed Equilibrations of Endocyclic and Exocyclic Olefins", Apr. 1960.
E. Vedejs, et al., Organic Syntheses, vol. 65, pp. 224–229, "(–)-α-Pinene by Isomerization of (–)-β-Pinene", 1987.
J. W. Batty, et al., J. Chem. Soc., vol. 44, pp. 175–179, "The Action of the Oppenauer Reagent on Primary Alcohols, Including Vitamin–A", 1938.
C. H. Heathcock, et al., J. Am. Chem. Soc., vol. 104, No. 4, pp. 1054–1068, "Total Synthesis of Lycopodium Alkaloids: (±)–Lycopodine, (±)–Lycodine, and (±)–Lycodoline", 1982.
Y. Ishii, et al., J. Org. Chem., vol. 51, No. 2, pp. 240–243, "Meerwein–Ponndorf–Verley Type Reduction of Ketones and Oppenauer Type Oxidation of Alcohols Under the Influence of $Co_2ZrH_2$", 1986.

* cited by examiner

Primary Examiner—Stanley S. Silverman
Assistant Examiner—Edward M. Johnson
(74) Attorney, Agent, or Firm—Oblon, Spivak, McClelland, Maier & Neustadt, P.C.

(57) ABSTRACT

A composite which is easy to manufacture and has excellent catalytic activity and mechanical strength is obtained by heating and drying a mixture of a carrier in powder form and a metal hydroxide in powder form or in molten form under a gas flow or under reduced pressure. The composite can be used as a catalyst for the isomerization of an olefin or for the oxidation reaction of an alcohol.

27 Claims, 4 Drawing Sheets

COMPOSITE AND MANUFACTURING METHOD THEREOF

BACKGROUND OF THE INVENTION

1. Field of the Invention

The present invention relates to a composite made of a carrier and a metal hydroxide, useful for an adhesive, a cleaning agent, a soap additive, a catalyst, an acid substance absorbent, an active carbon material, a deodorant material and a water purification agent and a manufacturing method thereof.

2. Discussion of the Background

A method for producing an oxidation catalyst in which a heat resistant inorganic substance such as silica or alumina, and an active carbon are compacted is known. The method results in a catalyst having excellent acid activity (Japanese Published Unexamined Patent Application No. Sho 49-123490). This catalyst can be obtained by subjecting heat resistant inorganic substance particles, preferably having a mean particle size of 1000 Å to 1.0 mm, and a carbon powder, preferably having a mean particle size of 100 Å to 1.0 mm, to a carbonization treatment at a temperature of 500° C. to 1000° C. under a flow of an inert gas. The catalyst is used for the oxidation of sulfur dioxide for flue-gas desulfurization, the oxidation of phenols, the oxidation of $Fe^{2+}$ in an aqueous solution, and the oxidative dehydrogenation of alcohols.

However, even if the activity is further increased, or for example, a metal hydroxide is added, in order to extend the use to other applications, such as the isomerization reaction of an olefin, the expected large effect is not exerted. On the other hand, a method for mixing and compounding a carrier and an inorganic substance is known in which an aqueous solution of a metal hydroxide or the like is added to the carrier, and then the solvent is evaporated to dryness (Supplementary Volume to Shokubai Koza (Catalytic Course), Catalytic Experiment Handbook, edited by Catalysis Society of Japan, (1986), vol. 11, p. 15). If a composite is prepared by applying this method it exhibits the properties of the metal hydroxide used. Therefore, the composite is susceptible to moisture, and hence it has a considerably low storage stability. In addition, its preparation is complicated. Further, the expected high catalytic activity cannot be obtained.

SUMMARY OF THE INVENTION

In view of the foregoing, it is therefore an object of the present invention to provide a composite made of a carrier and a metal hydroxide. It is another object of the present invention to provide an easy method for producing the composite. It is yet another object to provide a catalytic reaction using the composite.

This and other objects have been achieved by the present invention the first embodiment which includes a composite which is obtained by heating and drying of a mixture of a carrier in powder form, and a metal hydroxide in powder form or in molten form.

In another embodiment the present invention relates to a method for manufacturing a composite, comprising: mixing a carrier in powder form and a metal hydroxide in powder form and heating and drying the resulting mixture under a gas flow or under reduced pressure.

DETAILED DESCRIPTION OF THE INVENTION

The present inventors have conducted an intensive study to achieve the objects of the present invention. In accordance with one aspect of the present invention, a composite is provided that is obtained by heating and drying a mixture of a carrier in powder form and a metal hydroxide in powder form or in molten form. Further, in accordance with another aspect of the present invention, a method for manufacturing a composite is provided which includes mixing a carrier in powder form and a metal hydroxide in powder form, and heating and drying the mixture under a gas flow or under reduced pressure. The composite of the present invention can be preferably used for a catalytic reaction such as the isomerization reaction of an olefin or the oxidation reaction of alcohols described below.

As the isomerization catalyst for an olefin, a mixture of p-toluene sulfonic acid and acetic acid is known (J. Am. Chem. Soc., 82 (1960) p. 1750). If an olefin is isomerized by using this catalyst, oligomerization of the olefin is inevitable, and the yield is low. Further, it is also known that a base catalyst such as a mixture of ethylenediamine and potassium ethylenediamine amide is used as isomerization catalyst of an olefin (Organic Synthesis, 65 (1986) p. 224). This method uses a highly irritating diamine, and hence it presents a problem.

The following methods are known in which as the oxidation catalysts for alcohols a carbonyl compound is used as a hydrogen acceptor: (1) a method in which acetone is used as a hydrogen acceptor, and tri-t-butoxy aluminium is used as a catalyst (J. Chem. Soc., 44 (1938) p. 175); (2) a method in which benzophenone is used as a hydrogen acceptor, and t-butoxy potassium is used as a catalyst (J. Am. Chem. Soc., 104 (1982) p. 1054); (3) a method in which benzophenone is used as a hydrogen acceptor, and potassium hydride is used as a catalyst (J. Am. Chem. Soc., 104 (1982) p. 1054); and (4) a method in which benzaldehyde is used as a hydrogen acceptor and dicyclopentadione zirconium dihydride is used as a catalyst (J. Org. Chem. 51 (1986) p. 240). However, for any of the catalysts in the methods (1) to (4), the control of the moisture is difficult, and hence the catalyst is difficult to store. Further, for the metal hydride such as the catalyst in the method (3), ignition may occur due to the moisture in the solvent making this method risky. In addition, in the method (1), if water is added after completion of the reaction, an aluminium hydroxide gel forms. Accordingly, the post-treatment of the reaction becomes very difficult. Also, the catalyst in the method (4) is very expensive.

However, according to the composite product of the present invention, it is possible to avoid the above described oligomerization in the isomerization reaction of olefins. Therefore, the yield is high, and the composite product is safe. On the other hand, in the oxidation reaction of alcohols, the above problems of storage of the catalyst, safety and post-treatment of the reaction do not occur.

The carrier to be used in the present invention is not particularly limited. For example, porous materials are preferably used. Among such porous materials, heat-resistant inorganic substances and carbonaceous materials are preferred. Preferred heat-resistant inorganic substances include silica gel, alumina, silica-alumina, titanium oxide, magnesia, and zirconium oxide. Silica or alumina are particularly preferred. The carbonaceous materials have no particular restriction as long as they become carbonized by heating. Preferred examples of carbonaceous materials include coal, petroleum, the infusibilized product or heat-treated product after infusibilization of a synthetic pitch, active carbon, coke infusibilized product, and thermosetting resins. Particularly referred are coal, petroleum, the infusibilized product or heat-treated product after infusibilization of a synthetic pitch, or an active carbon. Especially when the active carbon is used, it is possible to broaden the range of application to a deodorant, a water purification agent, and an adsorbent by further treating it, and increasing the specific surface area.

Commonly commercially available metal hydroxides may be used as the metal hydroxides used in the present invention. Preferred examples of such metal hydroxides include lithium hydroxide, sodium hydroxide, potassium hydroxide, magnesium hydroxide, calcium hydroxide, aluminium hydroxide, and zirconium hydroxide. Sodium hydroxide and potassium hydroxide are particularly preferred from the viewpoint of operability.

In the present invention, the carrier and the metal hydroxide are mixed, and heated and dried to form a composite product. The mean particle size of the carrier before mixing is preferably set at 0.1 mm or less in terms of compatibility. The mean particle size of the metal hydroxide is preferably set at 1 mm or less for the same reason. Further, the metal hydroxide may also be previously molten before mixing with the carrier, and then used. The mixing ratio between the carrier and the metal hydroxide differs according to the property of the carrier. However, it is desirable that the metal hydroxide is mixed in an amount of 1 part by weight to 1000 parts by weight, and from the viewpoint of operability, in an amount of 10 parts by weight to 500 parts by weight, and more preferably in an amount of 50 parts by weight to 400 parts by weight, per 100 parts by weight of the carrier. The amount of metal hydroxide includes all values and subvalues therebetween, especially including 50, 100, 150, 200, 250, 300, 350, 400, 450, 500, 550, 600, 650, 700, 750, 800, 850, 900 and 950 parts by weight per 100 parts by weight of the carrier.

The composite of the present invention is preferably manufactured in the following manner. First, a carrier in powder form and a metal hydroxide in powder form are mixed, and heated under a gas flow or under reduced pressure. Such fine carrier and metal hydroxide in powder form are easily wetted at low temperature. Such wetting is accomplished under a gas flow or under reduced pressure. Therefore, drying is also effected at the same time. As the gas, air or an inert gas are preferably used. As the inert gas, nitrogen, argon, or the like are used. Air and an inert gas may be mixed.

A composite of the present invention for which no peak derived from the metal hydroxide crystals is present in the X-ray diffraction intensity curve is preferred because of its higher catalytic activity. Further, a composite which has been well dried, for which no background peak derived from water is present is preferred because of its higher mechanical strength. The X-ray intensity curve of the composite can be determined in the following manner. By using a rotating anode type X-ray diffractometer RINT 2400 manufactured by Rigaku Corporation, the X-ray measurement is carried out under the measuring conditions of a symmetrical reflection technique at 40 kV 100 mA, with a CuK α ray ($\lambda$=1.5405 Å), at a slit width of ½ deg, ½ deg, 0.15 mm, a scanning speed of 1 deg/min. Then, the same measurement is carried out, except that the sample is not placed in the diffractometer to determine the scattering intensity of air. Then, the scattering intensity of air is subtracted from the previously measured value.

In the present invention, the wording "no peak derived from metal hydroxide crystals is present" denotes as follows: when the X-ray intensity curve of the composite is measured under the foregoing conditions, no peak derived from the metal hydroxide crystals is detected in the peak data. The wording "no background peak derived from water is present" denotes as follows: when the X-ray intensity curve of the composite is measured under the foregoing conditions, the base line does not noticeably vary.

Figure 1:
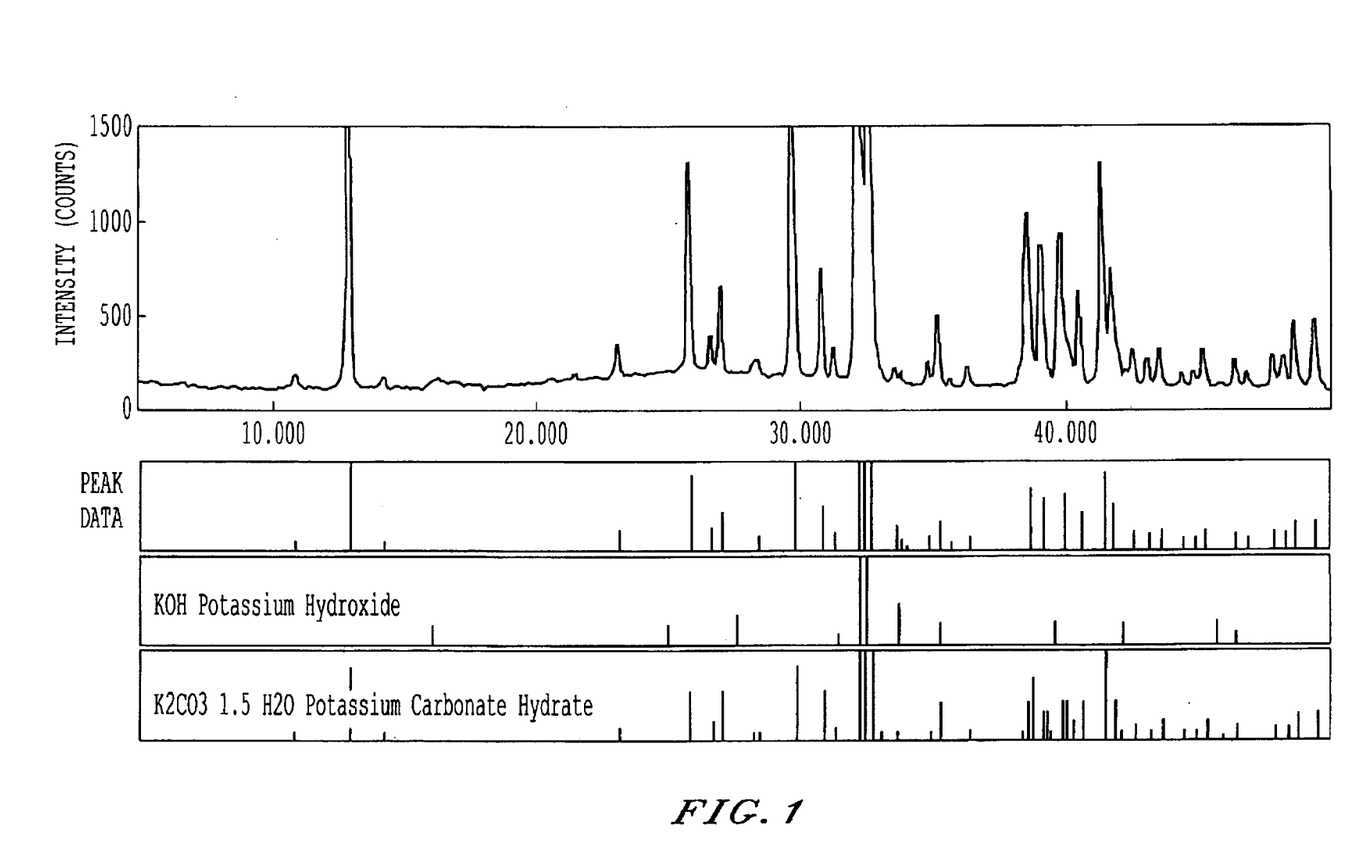
FIG. 1 shows the X-ray diffraction intensity curve of a composite obtained in Example 1.
Figure 2:
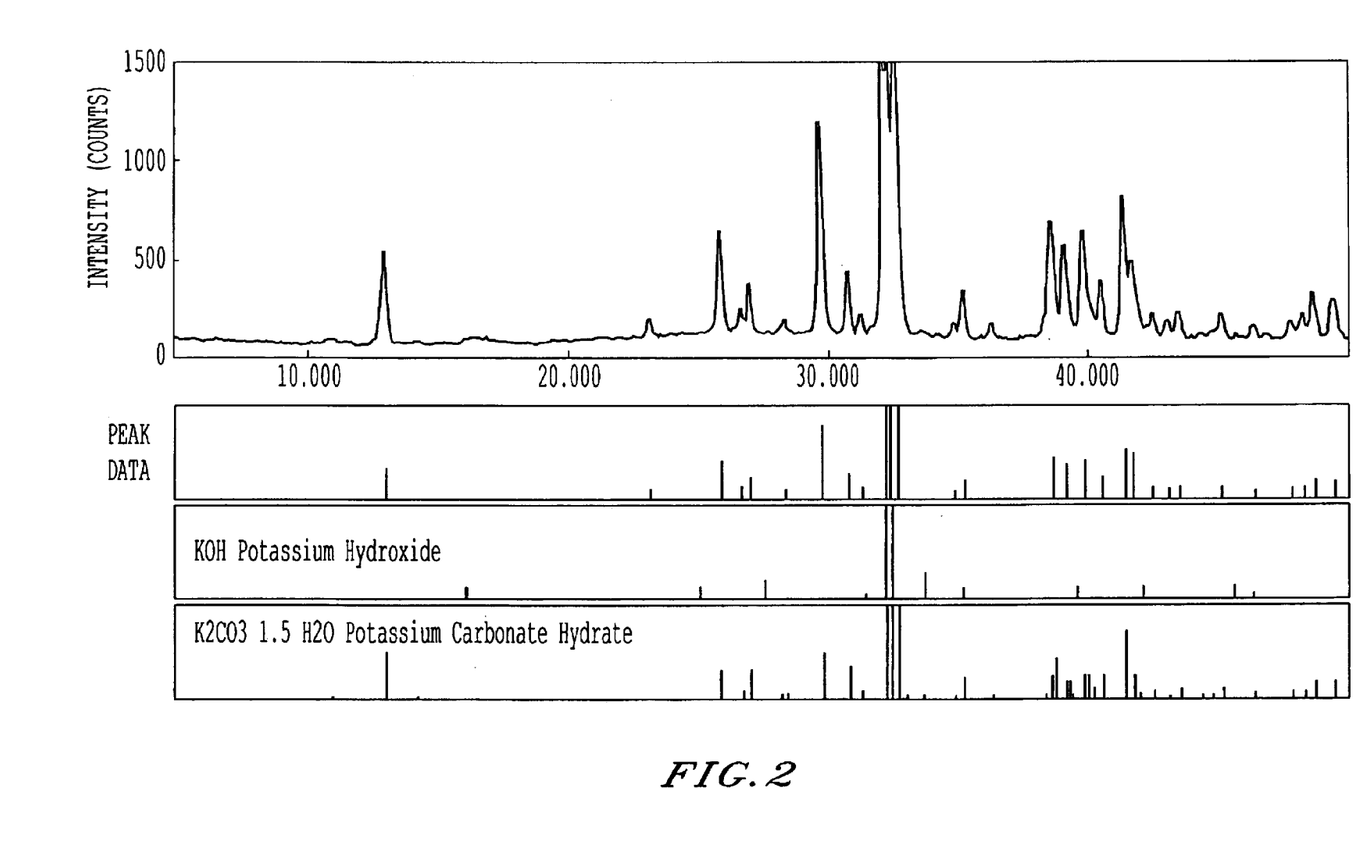
FIG. 2 shows the X-ray diffraction intensity curve of a composite obtained in Example 2.

FIGS. 1 and 2 are graphs, each showing an example of the X-ray intensity curve of the composite in which there are neither a peak derived from the metal hydroxide (KOH) crystals, nor a background peak derived from water. In each of FIGS. 1 and 2, the chart in the uppermost column shows a curve determined by actual measurement of the X-ray intensity of the composite, and the chart in the second column expresses this as peak data. Further, the chart in the third column shows the peak data inherently possessed by KOH. Therefore, if the peak data of the composite and the peak data inherently possessed by KOH FIG. 1 or 2 are compared, and no peak in agreement with the peak derived from KOH is present in the peak data of the composite, it is possible to judge that no peak derived from KOH is present for the composite.

Figure 3:
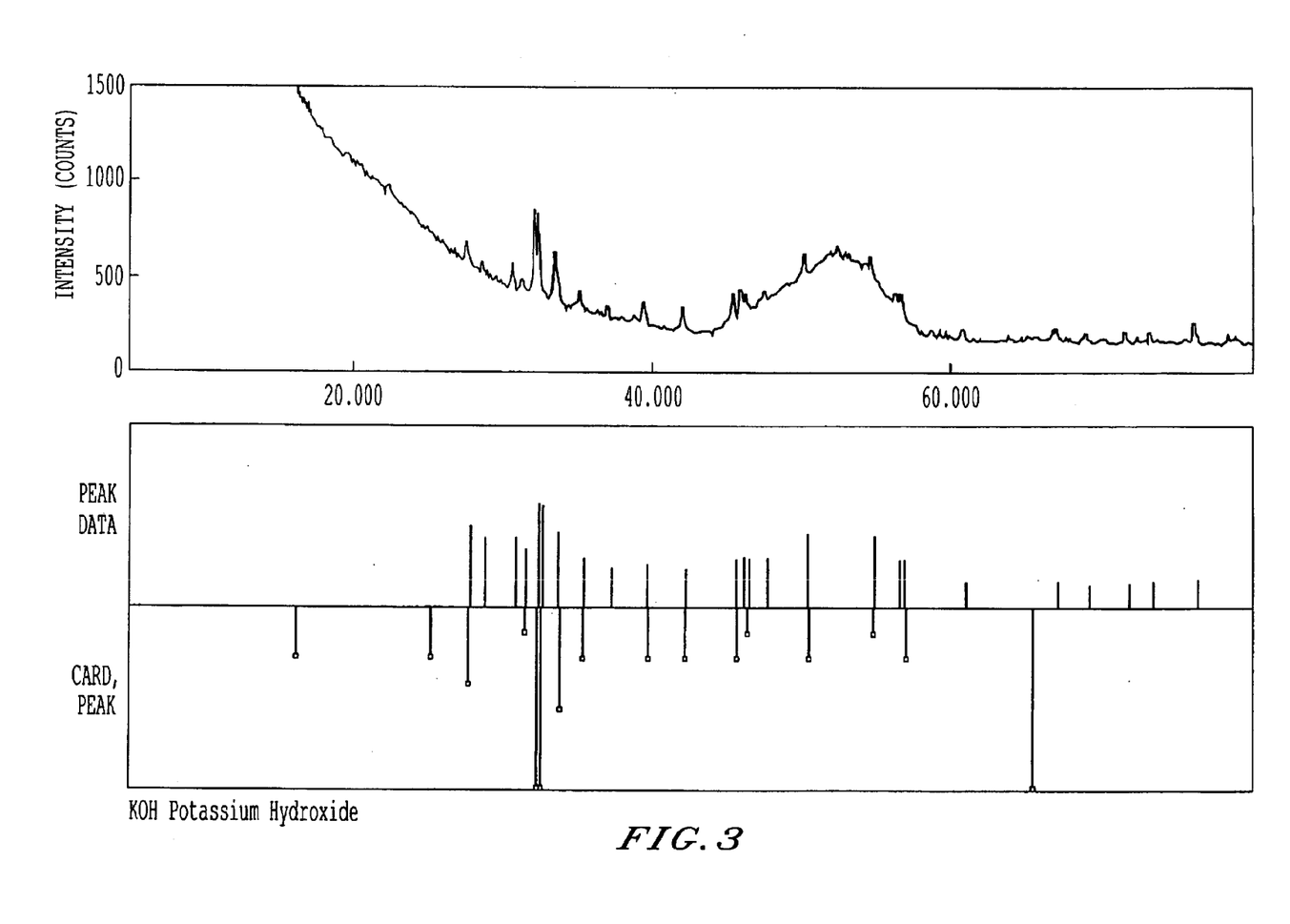
FIG. 3 shows the X-ray diffraction intensity curve of a composite obtained in Comparative Example 1.
Figure 4:
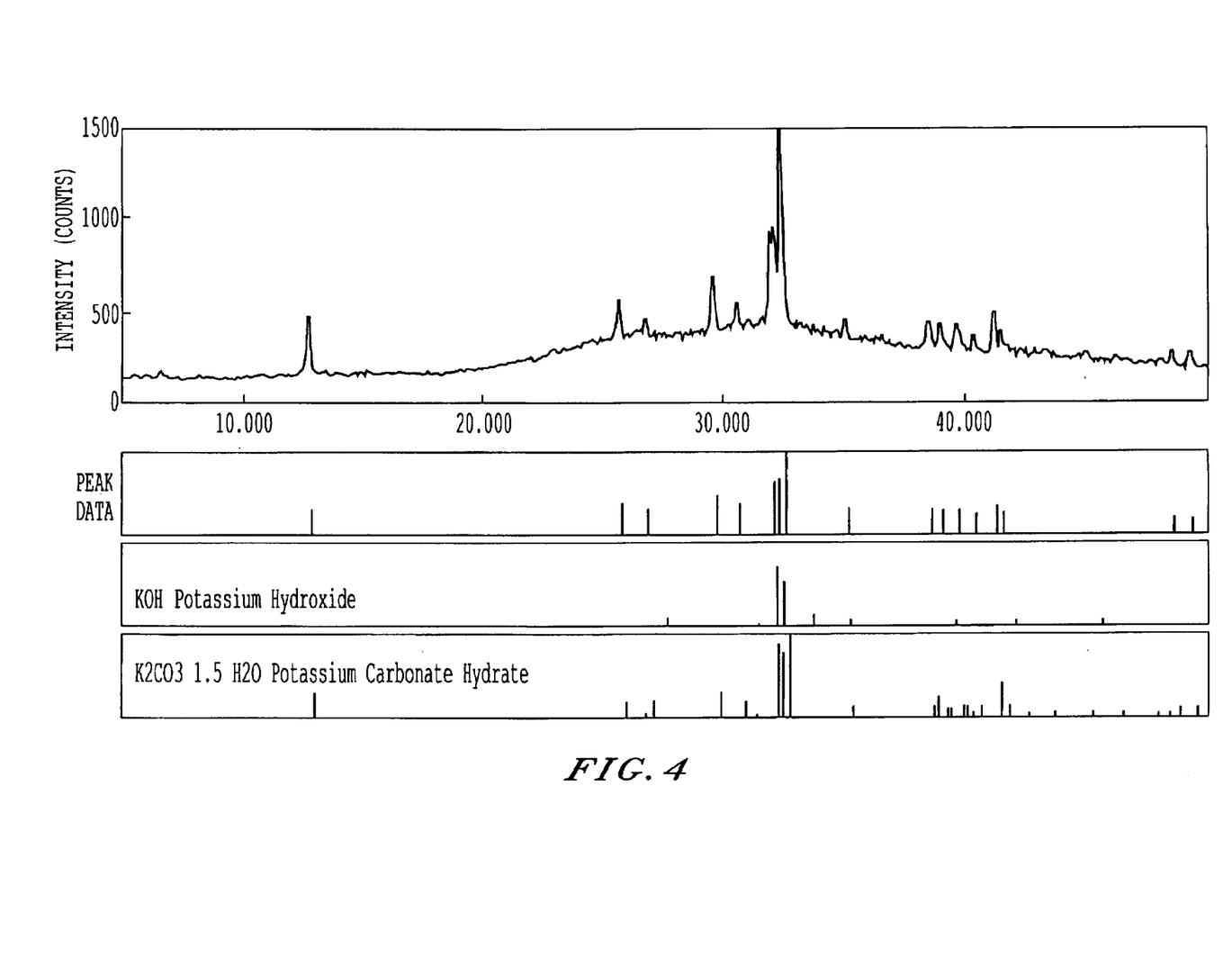
FIG. 4 shows the X-ray diffraction intensity curve of a composite obtained in Example 16.

In each of FIGS. 3 and 4, the base line of the X-ray intensity curve gently varies. This indicates that the background peak derived from water is present for the composite. Incidentally, FIGS. 3 and 4 are the graphs each showing the example in which the peak derived from KOH is present, as apparent from the comparison between the peak data and the peak data derived from KOH.

The composite of the present invention exhibits excellent activities in various catalytic reactions as apparent from the Examples described below. A distinct explanation of the reason for this cannot be exactly given. However, from the result of the measurement of the X-ray diffraction intensity curve, it can be considered as follows. The composite for which the peak derived from metal hydroxide crystals and the background peak from water are not present provides more excellent catalytic activity. By powdering the carrier and the metal hydroxide, it is possible to reduce the melting temperature. As a result, the metal hydroxide changes into another form, and it is uniformly dispersed on the carrier surface, so that the composite exhibits high catalytic activity.

If the temperature for heating the mixture in the present invention is too low, the catalytic activity is not very large. Therefore, heating is preferably carried out at 80° C. or more. However, if heating is carried out at 200° C. or more, the catalytic activity is reduced when the composite of the present invention is used as an isomerisation catalyst for olefins. On the other hand, the temperature may exceed 200° C. if the composite of the present invention is used as a catalyst for the oxidation reaction of alcohols. However, if the temperature exceeds 400° C., the catalytic activity tends to be reduced for oxidation of alcohols.

The method for manufacturing the composite of the present invention is characterized in that a mixture of a carrier in powder form and a metal hydroxide in powder form or in molten form is heated and dried at the same time. The drying is carried out in the presence of an inert such as nitrogen or argon, or in the presence of air, or in the presence of a mixture of an inert gas and air.

The drying step is preferably carried out at a gas flow rate of 1 mL/min to 100 L/min (mL: milliliter, L: liter) for every 100 parts by weight of the mixture of the carrier and the metal hydroxide. In view of the effect of drying and the cost efficiency, it is carried out at a flow rate of preferably 100 mL/min to 50 L/min, and more preferably 500 mL/min to 20 L/min. The gas flow rate includes all values and subvalues therebetween, especially including 30, 40, 50, 100, 150, 200, 250, 300, 350, 400 and 450 mL/min per 100 parts by weight of the mixture of carrier and metal hydroxide.

The gas flow may have a certain degree of moisture content. However, the relative humidity at 21° C. is preferably 60% or less, and in view of the efficiency of drying, it is more preferably 50% or less. As described above, in the present invention, it is possible to carry out the drying step not only under a gas flow, but also under reduced pressure. The value of the reduced pressure is generally 70 kPa or less. In view of the efficiency of drying, the drying step is carried out preferably at 40 kPa or less. Further, in the present invention, it is also possible to carry out the step through combination of drying under a gas flow and drying under reduced pressure.

The composite product of the present invention effectively functions as an isomerization catalyst for an olefin. Examples of such an olefin may include 1-butene, cis-2-butene, trans-2-butene, 1-pentene, E-2-pentene, Z-2-pentene, 1-hexene, E-2-pentene, Z-2-hexene, 1-octene, E-3-octene, Z-3-octene, 2,3-dimethyl-1-butene, 3,3-dimethyl-2-butene, 1-methyl-1-cyclohexene, 1-methyl-2-cyclohexene, 1-exomethylene cyclohexene, 1-phenyl-1-propene, 3-phenyl-1-propene, E-1-phenyl-1-butene, Z-1-phenyl-1-butene, E-1-phenyl-2-butene, Z-1-phenyl-2-butene, 4-phenyl-1-butene, 3,4-dihydrofuran, 2,5-dihydrofuran, 3,4-dihydro-2H-pyrane, 4-methyl-3,4-dihydro-2H-pyrane and 4-methyl-3,6-dihydro-2H-pyrane.

When the composite of the present invention is used as a catalyst for the isomerization reaction of an olefin, the amount of the composite to be used has no particular restriction. However, the composite is preferably used in an amount of 0.01 parts by weight to 100 parts by weight, and in view of the cost efficiency, the operability, and the reaction rate, preferably in the range of 0.1 parts by weight to 10 parts by weight, per 100 parts by weight of the olefin. The amount of composite includes all values and subvalues therebetween, especially including 0.05, 0.1, 0.15, 0.2, 0.25, 0.5, 1, 5, 10, 15, 20, 25, 30, 35, 40, 45, 50, 55, 60, 65, 70, 75, 80, 85, 90 and 95 parts by weight per 100 parts by weight of the olefin.

The composite of the present invention may be used as a catalyst for the oxidation reaction of alcohols using a carbonyl compound as a hydrogen acceptor. Preferred examples of the alcohols include secondary alcohols such as isopropanol, 2-butanol, 2-octanol, cyclohexanol, 1-phenyl-1-ethanol, and benzhydrol; primary allyl alcohols such as allyl alcohol, methallyl alcohol, crotyl alcohol, prenol, 2-cyclopenten-1-ol, 2-cyclohexen-1-ol, nerol, geraniol, 2,7-octadiene-1-ol, and cinnamic alcohol; and cyclic hemiacetals such as 2-hydroxy-tetrahydrofuran, 2-hydroxytetrahydropyrane, and 4-methyl-2-hydroxytetrahydropyrane.

Preferred examples of the carbonyl compound usable as hydrogen acceptor include aldehydes such as trimethylacetoaldehyde and benzaldehyde; and ketones such as acetone, methyl ethyl ketone, methyl isobutyl ketone, and benzophenone.

For carrying out the oxidation of alcohols, the mixing ratio between the carbonyl compound and the alcohol is preferably in a mixing ratio 1 to 10000 parts by weight of the carbonyl compound per 100 parts by weight of the alcohol. In view of the efficiency of oxidation and the volume efficiency of the reaction, the oxidation reaction is carried out preferably in a mixing ratio in the range of 50 to 5000 parts by weight, and more preferably in the range of 100 to 3000 parts by weight of the carbonyl compound, per 100 parts of alcohol. The mixing ratio includes all values and subvalues therebetween, especially including 5, 50, 100, 500, 1000, 1500, 2000, 2500, 3000, 3500, 4000, 4500, 5000, 5500, 6000, 6500, 7000, 7500, 8000, 8500, 9000 and 9500 parts of carbonyl compound 100 parts of alcohol.

The amount of the composite to be used for oxidation in the present invention has no particular restriction. However, the composite is preferably used in an amount of 0.001 to 100 parts by weight, and in view of the cost efficiency, operability, and reaction rate, in an amount of 0.01 to 10 parts by weight, per 100 parts by weight of the alcohol. The amount of composite for oxidation includes all values and subvalues therebetween, especially including 0.005, 0.01, 0.05, 0.1, 0.5, 1.5, 10, 15, 20, 25, 30, 35, 40, 45, 50, 55, 60, 65, 70, 75, 80, 85, 90 and 95 parts by weight per 100 parts by weight of the alcohol.

The form of the composite of the present invention when used for the isomerization reaction of an olefin, or the oxidation reaction of alcohols has no particular restriction. Thus, the composite may be used in various forms such as powder form, particle form, and tablet form. When the composite of the present invention is manufactured, a solvent is not necessarily required, but it may be used within such a range as not to inhibit the reaction. Examples of such a solvent include saturated hydrocarbons such as pentane, hexane, heptane, octane, decane, cyclohexane, methyl cyclohexane, and oyclooctane; and aromatic hydrocarbons such as benzene, toluene, xylene, and mesitylene. The solvent is preferably used in an amount of 1 part by weight to 10000 parts by weight, and in view of volume efficiency, operability, and cost efficiency, in an amount of 5 parts by weight to 500 parts by weight, per 100 parts by weight of the olefin. The amount of solvent includes all values and subvalues therebetween, especially including 5, 10, 50, 100, 500, 1000, 2000, 3000, 4000, 5000, 6000, 7000, 8000 and 9000 parts by weight per 100 parts by weight of the olefin.

The isomerization reaction of an olefin and the oxidation reaction of alcohols are carried out generally at 30° C. to 200° C., which varies according to the type of olefin or alcohol to be used. The reaction temperature includes all values and subvalues therebetween, especially including 40, 50, 60, 70, 80, 90, 100, 110, 120, 130, 140, 150, 160, 170, 180 and 190° C. As for the reaction pressure, the reaction is carried out generally under normal pressure. However, it is also possible to carry out the reaction under reduced pressure. As for the reaction method, it is also possible to carry out the reaction by a batch method using a stirring vessel. Alternatively, it is also possible to carry out the reaction by a continuous method such as a fixed bed or an isomerizing distillation method through a dispersed bed. Having generally described this invention, a further understanding can be obtained by reference to certain specific examples which are provided herein for purposes of illustration only, and are not intended to be limiting unless otherwise specified.

EXAMPLES

Example 1

Preparation of Composite 1

A 100 mL four-necked separable flask was equipped with a stirrer, a thermometer, and a gas inlet tube. Then, 10 g of silica gel (Si60 manufactured by Merck Co.), and 10 g of 95% potassium hydroxide crushed to an average particle size of 1 mm or less were charged therein, and dry nitrogen was introduced through the inlet tube into the flask at 200 mL/min. Heating was started in an oil bath heated to 120° C., and the temperature was increased up to 120° C. with slow stirring (revolutions per minute 50 rpm). After reaching 120° C., the temperature was increased at 10° C./min, so that the flask was heated up to 180° C. At 180° C., the flask was further heated and dried for another hour, and then cooled down to room temperature to obtain a composite.

By using a rotating anode type X-ray diffractometer RINT 2400 manufactured by Rigaku Corporation, the X-ray measurement is carried out under the measuring conditions of a symmetrical reflection technique at 40 kV 100 mA, with a CuK α ray ($\lambda$=1.5405 Å), at a slit width of ½ deg, ½ deg, 0.15 mm, a scanning speed of 1 deg/min. Then, the same measurement was carried out, except that the sample was not placed in the diffractometer to determine the scattering intensity of air. Then, the scattering intensity of air was subtracted from the X-ray diffraction intensity of the active carbon measured to determine the X-ray diffraction intensity curve. The results are shown in FIG. 1.

Example 2

Preparation of Composite 2

A 100 mL four-necked separable flask was equipped with a stirrer, a thermometer, and a gas inlet tube. Then, 10 g of an active carbon (PW manufactured by Kuraray Chemical Co., Ltd.), and 10 g of 95% potassium hydroxide crushed to an average particle size of 1 mm or less were charged therein, and dry air (21° C., relative humidity 20%) was introduced through the inlet tube into the flask at 200 mL/min. Heating was started in an oil bath heated to 120° C., and the temperature was increased up to 120° C. with slow stirring (revolutions per minute 50 rpm). After reaching 120° C., the temperature was increased at 10° C./min, so that the flask was heated up to 180° C. At 180° C., the flask was further heated and dried for another hour, and then cooled down to room temperature to obtain a composite. The X-ray diffraction intensity curve was determined in the same manner as in Example 1. The results are shown in FIG. 2.

Example 3

Preparation of Composite 3

A 100 mL three-necked separable flask was equipped with a stirrer and a thermometer. Then, 10 g of alumina (N611N manufactured by NIKKI Chemical CO., LTD.), and 20 g of 95% potassium hydroxide crushed to an average particle size of 1 mm or less were charged therein, and the pressure in the system was reduced to 20 kPa. Heating was started in an oil bath heated to 120° C., and the temperature was increased up to 120° C. with slow stirring (revolutions per minute 50 rpm). After reaching 120° C., the temperature was increased at 10° C./min, so that the flask was heated up to 190° C. At 190° C., the flask was further heated and dried for another two hours, and then cooled down to room temperature to obtain a composite.

Example 4

Preparation of Composite 4

A 100 mL three-necked separable flask was equipped with a stirrer, a thermometer, and a gas inlet tube. Then, 10 g of coal pitch (MPM-BL manufactured by ADCHEMCO Corporation), and 15 g of 95% potassium hydroxide crushed to an average particle size of 1 mm or less ware charged therein, and the pressure in the system was reduced to 20 kPa. Heating was started in an oil bath heated to 120° C., and the temperature was increased up to 120° C. with slow stirring (revolutions per minute 50 rpm). After reaching 120° C., the temperature was increased at 10° C./min, so that the flask was heated up to 180° C. At 180° C., the flask was further heated and dried for another three hours, and then cooled down to room temperature to obtain a composite.

Example 5

Preparation of Composite 5

In Example 1, after increasing the temperature to 120, the temperature was increased at 10° C./min, and the flask was heated up to 250° C. At 250° C., the flask was further heated and dried for another hour, and then cooled down to room temperature to obtain a composite.

Example 6

Preparation of Composite 6

In Example 2, after increasing the temperature to 120° C., the temperature was increased at 10° C./min, and the flask was heated up to 280° C. At 280° C., the flask was further heated and dried for another hour, and then cooled down to room temperature to obtain a composite.

Example 7

Preparation of Composite 7

In Example 4, after increasing the temperature to 120° C., the temperature was increased at 10° C./min, and the flask was heated up to 280° C. The heating source was changed from the oil bath to a salt bath, and the flask was further heated up to 360° C. At 360° C., the flask was further heated and dried for another hour, and then cooled down to room temperature to obtain a composite.

Example 8

Isomerization Reaction 1 of 2,3-Dimethyl-2-Butene

Into a 100 mL three-necked flask, 50 g of 2,3-dimethyl-2-butene and 0.5 g of the composite prepared in Example 1 were charged. The flask was then equipped with a distillation column packed with Helipacks to 20 cm in height, and with a reflux head and a thermometer, and the atmosphere in the system was replaced with nitrogen. The flask was heated to 84° C., and the distillate solution at an overhead temperature of 57° C. was collected. The entire contents of the flask were distilled for a reaction time of 8 hours to recover 49.1 g of 2,3-dimethyl-1-butene with a purity of 99.3%.

Example 9

Isomerization Reaction 2 of 2,3-Dimethyl-2-Butene

Into a 100 mL three-necked flask, 50 g of 2,3-dimethyl-2-butene and 0.5 g of the composite prepared in Example 2 were charged. The flask was then equipped with a distillation column packed with Helipacks to 20 cm in height, and with a ref lux head and a thermometer, and the atmosphere in the system was replaced with nitrogen. The flask was heated to 84° C., and the distillate solution at an overhead temperature of 57° C., was collected. The entire contents of the flask were distilled for a reaction time of 4 hours to recover 48.3 g of 2,3-dimethyl-1-butene with a purity of 99.7%.

Example 10

Isomerisation Reaction 1 of 4-Methyl-3,6-Dihydro-3H-Pyrane

Into a 100 mL three-necked flask, 70 g of 4-methyl-3,6-dihydro-2H-pyrane and 1.0 g of the composite prepared in Example 3 were charged. The flask was then equipped with a distillation column packed with Helipacks to 20 cm in height, and with a ref lux head and a thermometer, and the atmosphere in the system was replaced with nitrogen. The flask was heated to 120° C., and the distillate solution at an overhead temperature of 98° C. was collected. The entire contents of the flask were distilled for a reaction time of 12 hours to recover 66.3 g of 4-methylene-2H-pyrane with a purity of 93.7%.

Example 11

Isomerization Reaction a of 4-Methyl-3,6-Dihydro-2H-Pyrane

Into a 100 mL three-necked flask, 60 g of 4-methyl-3,6-dihydro-2H-pyrane and 1.2 g of the composite prepared in Example 4 were charged. The flask was then equipped with a distillation column packed with Helipacks to 20 cm in height, and with a ref lux head and a thermometer, and the atmosphere in the system was replaced with nitrogen. The flask was heated to 120° C., and the distillate solution at an overhead temperature of 98° C. was collected. The entire contents of the flask were distilled for a reaction time of 12 hours to recover 57.8 g of 4-methylene-2H-pyrane with a purity of 94.1%.

Example 12

Oxidation Reaction 1 of Prenol

Into a 300 mL three-necked flask, 150 g of toluene, 5 g of prenol, 1.5 g of the composite prepared in Example 5, and 30 g of bensophenone were charged with stirring at 60° C. for 3 hours. After 3 hours, the flask was cooled to room temperature, and the contents of the flask were analyzed by gas chromatography (GC-14A manufactured by Shimadzu Corp., column G-100 manufactured by Chemicals Evaluation and Research Institute, Japan, 70° C. to 210° C., temperature rising at 5° C./min). This analysis indicated that the conversion of prenol was 68 mol %, and that the selectivity to senecioaldehyde was 88 mol %.

Example 13

Oxidation Reaction 2 of Prenol

Into a 300 mL three-necked flask, 150 g of toluene, 5 g of prenol, 1.2 g of the composite prepared in Example 6, and 30 g of benzophenone were charged with stirring at 60° C. for 3 hours. After 3 hours, the flask was cooled to room temperature, and the contents of the flask were analyzed by gas chromatography (GC-14A manufactured by Shimadzu Corp., column G-100 manufactured by Chemicals Evaluation and Research Institute, Japan, 70° C. to 210° C., temperature rising at 5° C./min). This analysis indicated that the conversion of prenol was 77 mol %, and that the selectivity to senecioaldehyde was 91 mol %.

Example 14

Oxidation Reaction 2 of 2-Cyclohexene-1-ol

Into a 300 mL three-necked flask, 150 g of toluene, 5 g of 2-cyclohexene-1-ol, 1.6 g of the composite prepared in Example 7, and 20 g of benzophenone were charged with stirring at 60° C. for 2 hours. After 3 hours, the flask was cooled to room temperature, and the contents of the flask ware analyzed by gas chromatography (GC-14A manufactured by Shimadzu Corp., column G-100 manufactured by Chemicals Evaluation and Research Institute, Japan, 70° C. to 210° C., temperature rising at 5° C./min). This analysis indicated that the conversion of 2-cyclohexene-1-ol was 67 mol %, and that the selectivity to cyclohexenone was 91 mol %.

Example 15

Preparation of Composite 8, Isomerization Reaction 3 of 2,3-dimethyl-2-butene In Example 1, the temperature was set at 70° C. to obtain a composite. The isomerization reaction of 2,3-dimethyl-2-butene was carried out by using the composite in the same manner as in Example 8. As a result, it was indicated that the recovered 2,3-dimethyl-1-butene had a purity of 98.2% and a weight of 21.2 g.

Comparative Example 1

In Example 5, the active carbon and the potassium hydroxide were not powdered, and used in crushed form in pieces each with a size of about 3 mm to obtain a composite. The oxidation reaction of prenol was carried out by using the composite in the same manner as in Example 12. As a result, it was indicated that the conversion of prenol was 6 mol %, and that the selectivity to senecioaldehyde was 12 mol %. The X-ray diffraction intensity curve of the composite product was determined under the same conditions as in Example 1. The results are shown in FIG. 3.

Example 16

Preparation of Composite 9, Isomerization Reaction 4 of 2,3-dimethyl-2-butene In Example 5, the flask was heated to 70° C., and at 70° C., it was further heated and dried for another hour, and cooled to room temperature, to obtain a composite. The X-ray diffraction intensity curve of the composite product was determined under the same conditions as in Example 1. The results are shown in FIG. 4. The isomerization reaction of 2,3-dimethyl-2-butene was carried out by using the composite in the same manner as in Example 8. As a result, it was indicated-that the recovered 2,3-dimethyl-1-butene had a purity of 98.7% and a weight of 25.4 g.

In accordance with the present invention, it is possible to provide a composite obtained by heating and drying a mixture of a carrier in powder form and a metal hydroxide in powder form or in molten form at a low temperature. Such a composite is easy to manufacture, and has high catalytic activities, and is also excellent in mechanical strength. Therefore, it can be preferably used for the isomerization reaction of an olefin or for the oxidation reaction of alcohols.

Japanese patent application JP 35 649/2001 filed Feb. 13, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A composite which is obtained by heating and drying a mixture of a carrier in powder form, and a metal hydroxide in powder form or in molten form, wherein the heating is carried out at a temperature of not less than 80° C. to less than 400° C.; and the carrier comprises at least one selected from the group consisting of coal, an infusibilized product or heat-treated product after infusibilization of a synthetic pitch, and active carbon.

2. The composite according to claim 1, wherein the heating proceeds at a temperature of not less than 80° C. to less than 200° C.

3. The composite according to claim 1, wherein the heating proceeds at a temperature of not less than 200° C. to less than 400° C.

4. The composite according to claim 1, wherein the carrier is a porous material.

5. The composite according to claim 4, wherein the porous material is a heat resistant inorganic substance.

6. The composite according to claim 5, wherein the heat resistant inorganic substance is silica or alumina.

7. The composite according to claim 1, wherein the metal hydroxide is potassium hydroxide or sodium hydroxide.

8. The composite according to claim 1, wherein a mean particle size of the carrier before mixing is 0.1 mm or less, and a mean particle size of the metal hydroxide is 1 mm or less.

9. The composite according to claim 1, wherein the metal hydroxide is mixed in an amount of 1 to 1000 parts by weight per 100 parts by weight of the carrier.

10. The composite according to claim 1, wherein no peak derived from metal hydroxide crystals is present in an X-ray diffraction intensity curve of the composite.

11. The composite according to claim 1, wherein no background peak derived from water is present in an X-ray diffraction intensity curve of the composite.

12. The composite according to claim 1, which is a catalyst for an isomerization reaction of an olefin.

13. The composite according to claim 1, which is a catalyst for an oxidation reaction of alcohols.

14. A method for manufacturing a composite, comprising:

mixing a carrier in powder form and a metal hydroxide in powder form and heating and drying the resulting mixture under a gas flow or under reduced pressure, wherein the heating is carried out at a temperature of not less than 80° C. to less than 400° C., and the carrier comprises at least one selected from the group consisting of coal, an infusibilized product or heat-treated product after infusibilization of a synthetic pitch, and active carbon.

15. The method according to claim 14, wherein the gas is air, an inert gas or a mixture thereof.

16. The method according to claim 14, wherein the heating proceeds at a temperature of not less than 80° C. to less than 200° C.

17. The method according to claim 14, wherein the heating proceeds at a temperature of not less than 200° C. to less than 400° C.

18. The composite according to claim 1, wherein the heating is carried out at a temperature of not less than 80° C. to 380° C.

19. The method according to claim 14, wherein the heating is carried out at a temperature of from not less than 80° C. to 380° C.

20. The composite according to claim 1, wherein heating and drying is carried out in an inert gas flow and wherein the composite does not have a peak for the metal hydroxide in the X-ray diffraction intensity curve.

21. The method according to claim 14, wherein heating and drying are carried out under an inert gas flow and wherein the composite does not have a peak for the metal hydroxide in the X-ray diffraction intensity curve.

22. The composite according to claim 20, wherein the inert gas is at least one of nitrogen or argon.

23. The method according to claim 21, wherein the inert gas is at least one of nitrogen or argon.

24. A method comprising contacting an olefin with the composite of claim 1 to isomerize the olefin.

25. The method according to claim 24, wherein contacting includes heating the olefin in the presence of the composite.

26. A method comprising contacting an alcohol with the composite of claim 1 to oxidize the alcohol.

27. The method as claimed in claim 26, wherein contacting includes heating the alcohol in the presence of the composite.

* * * * *